(12) United States Patent
Vrba et al.

(10) Patent No.: US 7,998,088 B2
(45) Date of Patent: *Aug. 16, 2011

(54) GUIDEWIRE TIP CONSTRUCTION

(75) Inventors: Anthony Vrba, Maple Grove, MN (US); Brian R. Reynolds, Ramsey, MN (US); Brice Shireman, Maple Grove, MN (US)

(73) Assignee: Boston Scientifc Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/426,506

(22) Filed: Jun. 26, 2006

(65) Prior Publication Data

US 2006/0235337 A1 Oct. 19, 2006

Related U.S. Application Data

(63) Continuation of application No. 10/328,371, filed on Dec. 23, 2002, now Pat. No. 7,077,811.

(51) Int. Cl.
*A61B 5/00* (2006.01)
*A61M 25/00* (2006.01)

(52) U.S. Cl. ........................................................ 600/585

(58) Field of Classification Search ................. 600/585, 600/433–435; 623/1.35; 606/191
See application file for complete search history.

(56) References Cited

U.S. PATENT DOCUMENTS

| | | | |
|---|---|---|---|
| 4,538,622 A | 9/1985 | Samson et al. | |
| 4,763,647 A | 8/1988 | Gambale | |
| 4,811,743 A | 3/1989 | Stevens | |
| 4,922,924 A | 5/1990 | Gambale et al. | |
| 5,063,935 A | 11/1991 | Gambale | |
| 5,067,489 A | 11/1991 | Lind | |
| 5,144,959 A | 9/1992 | Gambale et al. | |
| 5,211,636 A | 5/1993 | Mische | |
| 5,228,453 A | 7/1993 | Sepetka | |
| 5,253,653 A | 10/1993 | Daigle et al. | |
| 5,345,945 A | 9/1994 | Hodgson et al. | |
| 5,376,083 A | 12/1994 | Mische | |
| 5,411,476 A | 5/1995 | Abrams et al. | |
| 5,488,959 A | 2/1996 | Ales | |
| 5,498,250 A | 3/1996 | Prather | |
| 5,546,948 A | 8/1996 | Hamm et al. | |
| 5,551,444 A | 9/1996 | Finlayson | |
| 5,605,162 A | 2/1997 | Mirzaee et al. | |
| 5,666,969 A | 9/1997 | Urick et al. | |
| 5,676,696 A * | 10/1997 | Marcade ...................... | 623/1.35 |
| 5,706,826 A | 1/1998 | Schwager | |
| 5,720,300 A | 2/1998 | Fagan et al. | |
| 5,772,609 A | 6/1998 | Nguyen et al. | |
| 5,797,856 A | 8/1998 | Frisbie et al. | |

(Continued)

FOREIGN PATENT DOCUMENTS

EP    0 274 412 A2    7/1988

(Continued)

*Primary Examiner* — Max Hindenburg
*Assistant Examiner* — Brian Szmal
(74) *Attorney, Agent, or Firm* — Seager, Tufte & Wickhem LLC

(57) ABSTRACT

Guidewire with an improved distal end. A guidewire with an improved distal end may include a core wire, a solder tip disposed at a distal end of the core wire, a radiopaque inner coil coupled to the distal end of the core wire, an outer coil disposed along the length of the core wire, and a distal hub coupled to the core wire and disposed proximate a distal end of the inner coil.

9 Claims, 3 Drawing Sheets

U.S. PATENT DOCUMENTS

| | | |
|---|---|---|
| 5,891,055 A | 4/1999 | Sauter |
| 5,957,903 A | 9/1999 | Mirzaee et al. |
| 6,039,699 A | 3/2000 | Viera |
| 6,039,743 A | 3/2000 | Quiachon et al. |
| 6,113,557 A | 9/2000 | Fagan et al. |
| 6,183,420 B1 | 2/2001 | Douk et al. |
| 6,190,332 B1 | 2/2001 | Muni et al. |
| 6,217,567 B1 | 4/2001 | Zadno-Azizi et al. |
| 6,241,690 B1 | 6/2001 | Burkett et al. |
| 6,355,016 B1 | 3/2002 | Bagaoisan et al. |
| 6,375,629 B1 | 4/2002 | Muni et al. |
| 6,387,060 B1 | 5/2002 | Jalisi |
| 6,673,025 B1 | 1/2004 | Richardson et al. |
| 7,074,197 B2 * | 7/2006 | Reynolds et al. ............. 600/585 |
| 7,077,811 B2 * | 7/2006 | Vrba et al. .................... 600/585 |
| 2002/0042582 A1 | 4/2002 | Vrba et al. |
| 2003/0069521 A1 | 4/2003 | Reynolds et al. |
| 2004/0064069 A1 * | 4/2004 | Reynolds et al. ............. 600/585 |

FOREIGN PATENT DOCUMENTS

| EP | 0 744 186 A1 | 11/1996 |
|---|---|---|
| WO | 92/04072 A1 | 3/1992 |
| WO | 98/18516 A1 | 5/1998 |
| WO | 98/55016 A1 | 12/1998 |
| WO | WO0032265 | 6/2000 |

* cited by examiner

GUIDEWIRE TIP CONSTRUCTION

This application is a continuation of U.S. patent application Ser. No. 10/328,371 filed Dec. 23, 2002.

BACKGROUND OF THE INVENTION

1. Field of the Invention

The present invention pertains to guidewires for use with intravascular catheters. More particularly, the present invention pertains to guidewires with an improved distal tip.

2. Description of the Related Art

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

Intravascular catheters are commonly used in conjunction with a guidewire. A guidewire may be advanced through the patient's vasculature until it has reached a target location. Once in place, a catheter may be threaded onto the guidewire and urged distally until the distal end of the catheter reaches a target location.

The vasculature of a human being can be a very tortuous path. In order for a guidewire to be steered through the vasculature, it may be beneficial for the guidewire to be flexible, particularly near the distal end. Increased flexibility may be incorporated into a guidewire in a number of differing ways. For example, the guidewire may be manufactured from materials having a different flexibility, the distal tip may be tapered, etc.

In order to determine the location of the guidewire within the vasculature, a marker band may be coupled to the guidewire. The marker band may be fixedly attached to the distal tip of the guidewire so as to enable a clinician to accurately monitor the location of the guidewire.

BRIEF SUMMARY OF THE INVENTION

The present invention pertains to a refinement to guidewires. More particularly, the present invention pertains to a guidewire with an improved distal tip. Imaging the distal tip may allow the clinician to precisely direct the guidewire to a specific location within the vasculature while monitoring its location on, for example, a fluoroscopy screen.

The guidewire may comprise an elongate shaft having a proximal end and a distal end. A solder tip may be disposed at the distal end of the shaft. The radiopaque inner coil may be coupled to the distal end of the shaft proximate the solder tip. An outer coil may be disposed along the length of the shaft; a portion of the outer coil may be disposed over the inner coil. The distal end of the outer coil may be coupled to the solder tip.

The inner coil may be disposed between a distal hub and a proximal hub. The distal hub may be coupled to the shaft and disposed proximate the solder tip. The distal hub may serve as a physical barrier between the solder tip and the inner coil. The proximal hub may be coupled to the shaft and disposed proximate the proximal end of the inner coil. The proximal hub may substantially prevent the inner coil from moving proximally along the shaft. The inclusion of the proximal hub and the distal hub may allow the distal tip to have a desired level of flexibility in addition to a radiopaque coil that may be useful for imaging.

As an alternate to the inclusion of the proximal hub, the inner coil, the outer coil, or both may be coupled directly to the shaft. For example, the inner coil may be coupled to the shaft at a proximal end of the inner coil. Coupling the proximal end of the inner coil to the shaft may allow the guidewire to comprise a desired level of flexibility.

DETAILED DESCRIPTION OF THE INVENTION

Figure 1:
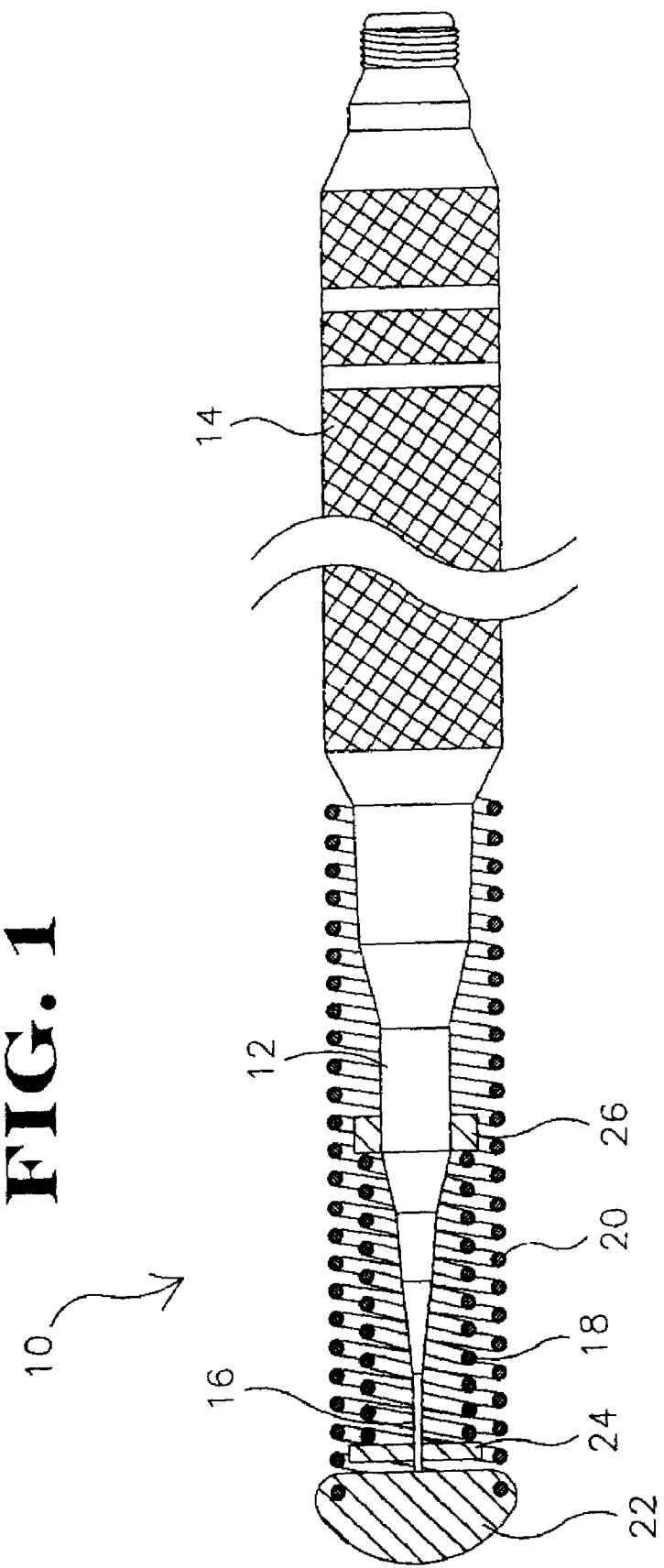
FIG. 1 is a cross-sectional view of an example distal tip of a guidewire.

The following description should be read with reference to the drawings wherein like reference numerals indicate like elements throughout the several views. The detailed description and drawings illustrate example embodiments of the claimed invention.

FIG. 1 is a cross-sectional view of the distal tip of a guidewire. A guidewire 10 comprises an elongate shaft or core wire 12 having a proximal end 14 and a distal end 16. An inner coil 18 may be disposed at distal end 16 of core wire 12 and an outer coil 20 may be disposed along the length of core wire 12. A portion of outer coil 20 is disposed over inner coil 18. A tip 22 such as a solder tip, may be formed on core wire 12 at distal end 16. A portion of outer coil 20 may be coupled to solder tip 22. A distal hub 24 is disposed proximate of solder tip 22.

Core wire 12 may be comprised of nickel-titanium alloy, stainless steel, a composite of nickel-titanium alloy and stainless steel. Alternatively, core wire 12 may be comprised of metals, polymers, combinations or composites thereof, or other suitable materials. Core wire 12, may be distally tapered. According to this embodiment, core wire 12 may include a plurality of distal segments or comprise a single, generally tapered distal end 16. Each distal segment may comprise a decreased outside diameter or individual segments may each taper along the length of a particular segment. A person of ordinary skill in the art could appreciate that a vast number of alternate configurations of segments and distal ends may be included without departing from the scope of the invention.

A portion of outer coil 20 may be embedded within solder tip 22. Embedded is understood to be disposed within, coupled to, set in, implanted, fixed, etc. Solder tip 22 may, thus, fix outer coil 20 relative to core wire 12. Alternatively, outer coil 20 may be soldered to core wire 12 proximate solder tip 22.

Distal hub 24 is coupled to core wire 12 and may be disposed proximate solder tip 22. More particularly, distal hub 24 may be disposed between solder tip 22 and inner coil 18. According to this embodiment, distal hub 24 may serve as a physical barrier between solder tip 22 and inner coil 18. This physical barrier may prevent inner coil 18 from becoming embedded within solder tip 22, particularly during manufacturing of guidewire 10 where molten or partially molten solder may migrate along core wire 12. Distal hub 24 may be comprised of polytetrafluoroethylene (PTFE) or other suitable materials.

Inner coil 18 may be radiopaque. A radiopaque coil is understood to be capable of producing a relatively bright image on a fluoroscopy screen or another imaging technique during a medical procedure. This relatively bright image aids the user of guidewire 10 in determining the location of distal end 16 of core wire 12. Radiopaque inner coil 18 may be comprised of a number of radiopaque materials including, but not limited to, gold, platinum, tungsten alloy, and plastic material loaded with a radiopaque filler. Guidewire 10 may further comprise additional radiopaque markers, for example near proximal end 14 of core wire 12. It should be understood that inner coil 18, alternatively, may comprise a plurality of individual coils that when taken together would have the same general physical characteristics as inner coil 18.

In addition to distal hub 24, guidewire 10 may further comprise a proximal hub 26. Inner coil 18 may extend along core wire 12 between distal hub 24 and proximal hub 26. Inner coil 18 may be disposed between distal hub 24 and proximal hub 26 without being permanently fixed to core wire 12 and be, thus, loosely disposed between distal hub 24 and proximal hub 26. Proximal hub 26 may also prevent inner coil 18 from moving proximally relative to core wire 12. By disposing inner coil 18 between distal hub 24 and proximal hub 26 without permanently fixing inner coil 18 to core wire 12, guidewire 10 may have increased flexibility. Increased flexibility may enhance the ability of a clinician to advance guidewire 10 through the vasculature.

Alternatives to the embodiment shown in FIG. 1 may include inner coil 18 having a portion that coupled to core wire 12, outer coil 20, distal hub 24, proximal hub 26, or combinations thereof. Inner coil 18 may be, for example, soldered to any one of the above elements at a singular location. According to these embodiments, inner coil 18 would be fixed in a manner that would result in only a minimum change in the overall flexibility of guidewire 10.

Proximal hub 26 may be comprised of polytetrafluoroethylene (PTFE). Alternatively, proximal hub 26 may be comprised of a heat shrink tube. In an exemplary embodiment, proximal hub 26 may be comprised of materials similar to those listed above.

The dimensions of inner coil 18 may include a length of about, for example, 0.1 inches to 1.8 inches and the coil may define an outside diameter of about, for example, 0.0080 inches to 0.0120 inches. According to an embodiment where inner coil 18 comprises a plurality of coils, spacing may occur between coils. The spacing may be a fixed distance of about, for example, 0.3 inches to 0.8 inches or the spacing may vary. The dimensions listed above are not intended to be limiting. Alterations to the dimensions of inner coil 18 may be incorporated without departing from the scope of the present invention.

Outer coil 20 may extend proximally from solder tip 22 along the length of core wire 12. Outer coil 20 may be brazed to proximal end 14 of core wire 12. Outer coil 20 may be comprised of a nickel-titanium alloy or stainless steel. Alternatively, outer coil 20 may be comprised of materials similar to those listed above. In addition, outer coil 20 may further comprise an outer silicone coating.

In at least some embodiments, it may be desirable to configure inner coil 18 and outer coil 20 so that they are wound or otherwise disposed about shaft 12 in differing or opposite directions. This feature is best seen and is described in accompanying description of FIG. 4.

Figure 4:
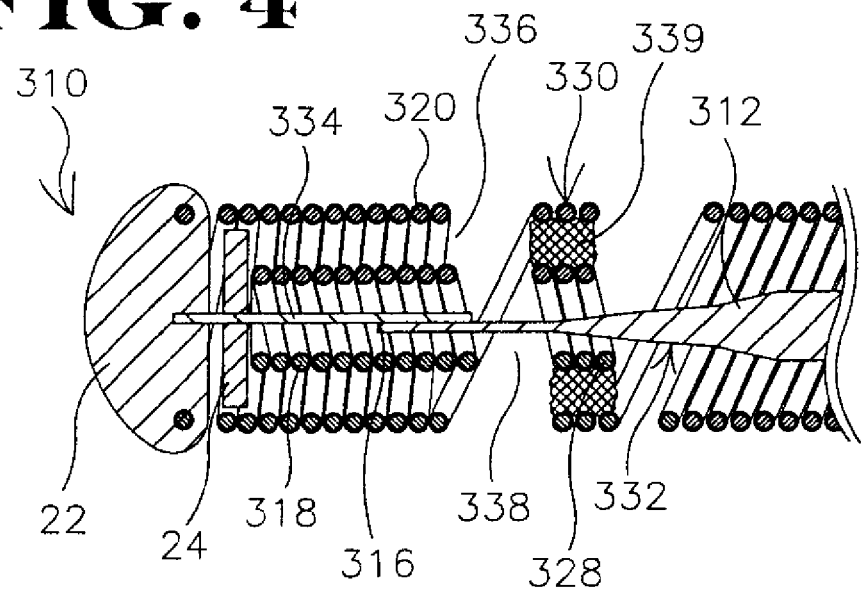
FIG. 4 is a cross-sectional view of the distal end of another example guidewire.
Figure 5:
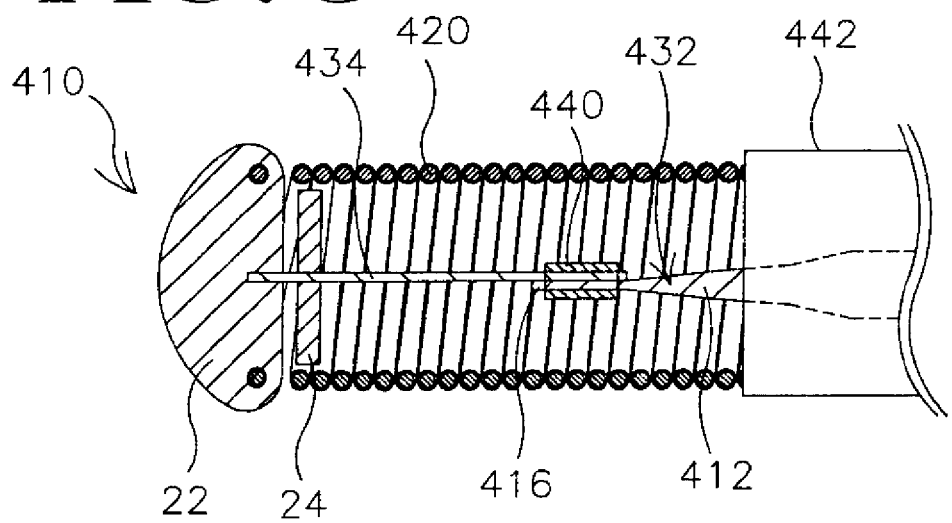
FIG. 5 is a cross-sectional view of the distal end of another example guidewire.

Guidewire 10 may further comprise additional features. For example, guidewire 10 may include one or more proximal marker bands. These marker bands may be disposed proximate proximal end 14 of core wire 12. In addition, a connector may be disposed at proximal end 14 of core wire 12 that may be used to couple an extension ribbon to guidewire 10 (as shown in FIGS. 4 and 5).

Figure 2:
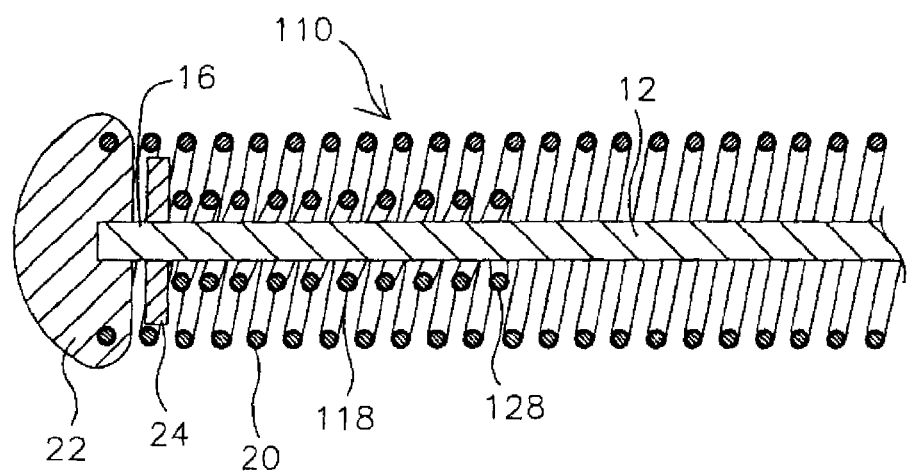
FIG. 2 is a cross-sectional view of the distal end of another example guidewire.

FIG. 2 is a cross-sectional view of the distal end of an alternate guidewire. Guidewire 110 is essentially similar to guidewire 10 except that inner coil 118 further comprises a proximal end 128 that may be coupled to core wire 12. The use of inner coil 118 may allow the omission of a proximal hub (i.e., proximal hub 26) as in guidewire 10. Alternatively, inner coil 118 may be used in conjunction with proximal hub 26.

Proximal end 128 may be coupled to core wire 12 by a number of methods. For example, proximal end 128 may be soldered to core wire 12. Alternatively, proximal end 28 may be heat bonded, coupled by a heat shrink tube, coupled by a polytetrafluoroethylene (PTFE), or other methods that may comprise a physical joining of proximal end 128 of inner coil 118 to core wire 12.

Coupling proximal end 128 to core wire 12, has a minimal impact on the flexibility of guidewire 110. Accordingly, proximal end 128 may be soldered to core wire 12 at a single point so as to minimize potential alterations in flexibility.

Figure 3:
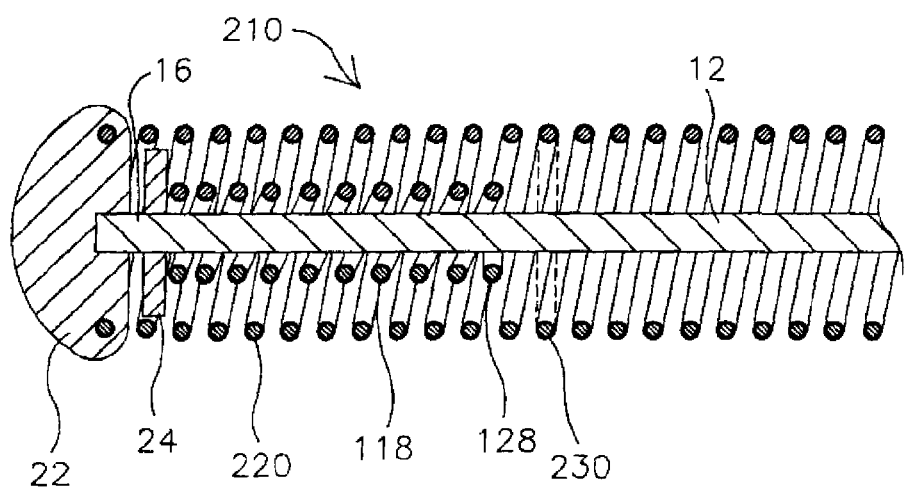
FIG. 3 is a cross-sectional view of the distal end of another example guidewire.

FIG. 3 is a cross-sectional view of the distal end of a second alternate guidewire. Guidewire 210 is essentially similar to guidewire 110 except that outer coil 220 further comprises a proximal region 230 that may be coupled to core wire 12. In alternative embodiments, outer coil 220 may be used in conjunction with inner coil 18, with proximal hub 26, or any of the embodiments described herein.

Proximal region 230 may be coupled to core wire 12 by a number of methods including those described above. For example, proximal region 230 may be soldered to core wire 12. Moreover, coupling of proximal region 230 may be used independently of inner coil 118 being soldered (or otherwise coupled) to core wire 12.

Another example guidewire 310 is illustrated in FIG. 4. Guidewire 310 is essentially the same in form and function as the other guidewires described herein, with a few exceptions as described below. Guidewire 310 includes shaft 312 that includes distal end 316. Shaft 312 may be comprised of metals, metal alloys, polymers, combinations thereof, and the like as described above in relation to shaft 12. For example, shaft 312 may be comprised of nickel-titanium alloy. In at least some embodiments, shaft 312 has a narrowed or tapered region 332 proximate distal end 316 similar to the tapered region shown in FIG. 1. The reduction in the thickness of shaft 312 adjacent tapered region 332 may, for example, may aid in the maintenance of or otherwise improve the distal flexibility of guidewire 310. Guidewire 310 may also include any of the other structures or structural features described herein. For example, guidewire 310 may include a proximal hub similar to hub 24.

In at least some embodiments, shaft 312 may be truncated or otherwise terminate at a location proximal to distal solder tip 22. A distal shaft or ribbon 334 may be coupled to distal end 316 of shaft 312 and extend between shaft 312 and solder tip 22. Ribbon 334 may be included to serve a number of purposes. For example, ribbon 334 may be comprised of a thin strip of stainless steel and may provide some additional structural support between the relatively rigid solder tip 22 and the relatively flexible distal end 316 of shaft 312. Additionally, it may be desirable to improve the bonding of a nickel titanium alloy structure (e.g., shaft 312) with a tin or tin-indium based solder structure (e.g., tip 22). According to this embodiment, ribbon 334 may be use to enhance the bonding of shaft 312 and tip 22. For example, ribbon 334 may be comprised of stainless steel so that one end can be attached to solder tip 22 and the other end may be attached to distal end 316 of shaft (e.g., by adhesive, welding, soldering, crimping, banding, mechanical bonding, etc.).

Guidewire 310 may also include an inner coil 318 and an outer coil 320 that are essentially the same in form and function as coils 18 and 20, respectively. For example, inner coil 318 may be comprised of, coated with, or otherwise include a radiopaque material and may be disposed adjacent distal end 316 of shaft. Distal hub 24 may be disposed adjacent the distal end of inner coil 318 in a manner similar to what is described above.

A number of couplings, connections, or attachments may join various combinations of inner coil 318, outer coil 320, and shaft 312 (and/or ribbon 334). For example, it may be desirable to attach outer coil 320 to inner coil 318. Alternatively, it may be desirable to join inner coil 318 to shaft 312, outer coil 320 to shaft 312, or to join all three components. The type of attachment may also vary. For example, the various combinations of components may be joined by an adhesive, by solder, by a weld, by a mechanical bond, or other suitable means. Moreover, the location of the connection may also be varied. For example, it may be desirable to join outer coil 320 and inner coil 318 at a location adjacent proximal end 328 of inner coil. It can be appreciated, however, that it may also be desirable to join any combination of the components adjacent proximal region 330 of outer coil 320, adjacent the distal ends of inner and outer coils 318/320, or at essentially any other suitable position along the length of guidewire 310.

In at least some embodiments, it may be desirable to alter the pitch of inner coil 318 and/or 320. For example, outer coil may include one or more increased pitch regions 336 and inner coil 318 may include also include one or more increased pitch regions 338. In embodiments where inner coil 318 and outer coil 320 are attached, it may be desirable join coils 318/320 adjacent the increased pitch regions 336/338. This arrangement may incorporate a number desirable features into guidewire 310. For example, if a solder joint 339 is used to join coils 318/320, including increased pitch regions 336/338 adjacent the joint may help to reduce or prevent the spreading or wicking of solder laterally from the joint. This feature is desirable because the wicking of solder may create stiff or generally less flexible regions of guidewire 310 that may interfere with the desired flexibility characteristics of guidewire 310.

Additionally, it may also be desirable to alter the direction of the winding of inner coil 318 and/or outer coil 320. For example, inner coil 318 may be wound in the opposite direction of outer coil 320. This feature may incorporate a number of desirable features into guidewire 310. For example, orienting the directions of the winding of coils 318/320 may help to reduce or prevent any nesting that may occur between coils 318/320. Reducing or eliminating the nesting between coils 318/320 may aid in the maintenance of the shape, profile, and integrity of guidewire 310.

Another example guidewire 410 that is similar to other guidewires described herein is illustrated in FIG. 5. Guidewire 410 includes shaft 412 that is essentially the same as shaft 312 and includes distal end 416 and tapered region 432. Guidewire 410 also includes outer coil 420. In some embodiments, outer coil 420 may be comprised of a radiopaque material such as platinum or any of those listed above. Alternatively outer coil 420 may be the same or similar to other outer coils described above.

Guidewire 410 may also include ribbon 434 that is essentially the same as ribbon 334 that extends between shaft 412 and distal solder tip 22. Ribbon 434 and shaft 412 may be attached similarly to what is described above such as by adhesives or mechanical bonds. In addition to or as an alternative to the above attachment, ribbon 434 may be coupled to shaft 412 by a connector 440. Connector 440 may comprise a variety of different structures suitable for connecting ribbon 434 and shaft 412. For example, connector 440 may comprise stainless steel hypodermic tubing. Alternatively, connector may be comprised of a nickel-chromium-iron alloy such as INCONEL 625, which advantageously welds to both stainless steels and nickel-titanium alloys. INCONEL 625 may be obtained from California Fine Wire Company of Grover Beach, Calif. It can be appreciated that connector 440 may be included in any other appropriate embodiments of the guidewires described herein without departing from the spirit of the invention.

In at least some embodiments, a sleeve 442 may be disposed over at least a portion of shaft 412. For example, sleeve 442 may be disposed over the portion of tapered region 432 located proximally of outer coil 420. According to this embodiment, sleeve may have a length in the range of about 10-45 centimeters (e.g., 30 centimeters) or longer. Sleeve 442 may be attached to shaft 412 in essentially any suitable manner, for example by an adhesive. Sleeve 442 may be comprised of a polymer such as polyurethane or any other suitable material including those listed above. Alternatively, sleeve 442 may be comprised of a polymer doped with radiopaque materials such as tungsten or tungsten alloys.

Similar to what is described above, a number of couplings, connections, or attachments may join any of the various combinations of outer coil 420, shaft 412, ribbon 434, connector 440, and sleeve 442. Also, the type of attachment and the location of the connection or connections may also be varied as described above. Additionally, guidewire 410 may also include other structural features described in relation to other embodiments such as an inner coil similar to those described herein or a proximal hub such as hub 24.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A guidewire comprising:
   an elongate shaft having a proximal end and a distal end;
   an atraumatic tip disposed at the distal end of the shaft;
   a distal stop comprising polytetrafluoroethylene disposed on the elongate shaft proximal of the atraumatic tip;
   a proximal stop comprising polytetrafluoroethylene disposed on the elongate shaft proximal of the distal stop;
   an inner coil disposed about the elongate shaft between the proximal stop and the distal stop; and
   an outer coil disposed about the elongate shaft and about the inner coil;
   wherein the inner coil is not fixedly secured directly to the elongate shaft;
   wherein the outer coil is wound about the elongate shaft in a first direction and the inner coil is wound about the elongate shaft in a second direction, and wherein the first direction is substantially opposite of the second direction.

2. The guidewire of claim 1, wherein the inner coil comprises a distal end disposed adjacent the distal stop and a proximal end disposed adjacent the proximal stop.

3. The guidewire of claim 1, wherein the elongate shaft comprises stainless steel, a nickel-titanium alloy or a composite of both.

4. The guidewire of claim 1, wherein the inner coil is radiopaque.

5. The guidewire of claim 1, wherein the inner coil comprises one of platinum, gold or tungsten alloy.

6. The guidewire of claim 1, wherein the outer coil comprises stainless steel or nickel-titanium alloy.

7. The guidewire of claim 1, wherein the outer coil comprises a distal end and a proximal end.

8. The guidewire of claim 7, wherein the outer coil distal end is coupled to the atraumatic tip.

9. The guidewire of claim 7, wherein the outer coil proximal end is coupled to the elongate shaft.

* * * * *